(12) United States Patent
Uenveren et al.

(10) Patent No.: US 8,338,651 B2
(45) Date of Patent: Dec. 25, 2012

(54) PREPARATION OF HALOGEN AND HYDROGEN CONTAINING ALKENES OVER METAL FLUORIDE CATALYSTS

(75) Inventors: Ercan Uenveren, Hannover (DE); Erhard Kemnitz, Berlin (DE); Stephan Rudiger, Rangsdorf (DE); Anton Dimitrov, Berlin (DE); Johannes Eicher, Sehnde (DE)

(73) Assignee: Solvay Fluor GmbH, Hannover (DE)

( * ) Notice: Subject to any disclaimer, the term of this patent is extended or adjusted under 35 U.S.C. 154(b) by 382 days.

(21) Appl. No.: 12/668,568

(22) PCT Filed: Jul. 11, 2008

(86) PCT No.: PCT/EP2008/059112
§ 371 (c)(1),
(2), (4) Date: Jan. 11, 2010

(87) PCT Pub. No.: WO2009/010472
PCT Pub. Date: Jan. 22, 2009

(65) Prior Publication Data
US 2010/0191024 A1    Jul. 29, 2010

(30) Foreign Application Priority Data

Jul. 13, 2007  (EP) ..................................... 07112445
Jul. 13, 2007  (EP) ..................................... 07112446

(51) Int. Cl.
*C07C 17/25*    (2006.01)
(52) U.S. Cl. .......................... 570/156; 570/151; 570/158
(58) Field of Classification Search .................. None
See application file for complete search history.

(56) References Cited

U.S. PATENT DOCUMENTS

| | | | |
|---|---|---|---|
| 2,673,139 A * | 3/1954 | Woolf et al. ................. | 423/489 |
| 3,941,874 A | 3/1976 | Payne | |
| 4,902,838 A | 2/1990 | Manzer et al. | |
| 5,559,069 A | 9/1996 | Rao et al. | |
| 5,880,315 A | 3/1999 | Rao et al. | |
| 6,093,859 A | 7/2000 | Nappa et al. | |
| 6,110,436 A | 8/2000 | Scholz et al. | |
| 6,262,321 B1 | 7/2001 | Nappa et al. | |
| 6,369,284 B1 * | 4/2002 | Nappa et al. ................. | 570/156 |
| 7,091,388 B2 | 8/2006 | Tung et al. | |
| 7,259,281 B2 * | 8/2007 | Du Boisson et al. ......... | 570/126 |
| 7,592,287 B2 * | 9/2009 | Kemnitz et al. ............... | 502/224 |
| 2006/0052649 A1 | 3/2006 | Kemnitz et al. | |
| 2008/0274037 A1 * | 11/2008 | Gross et al. ................... | 423/465 |

FOREIGN PATENT DOCUMENTS

| | | |
|---|---|---|
| EP | 0234002 A1 | 9/1987 |
| EP | 1440939 A1 | 7/2004 |
| EP | 1666411 A1 | 6/2006 |
| FR | 2710054 A1 | 3/1995 |
| WO | WO 2004/096737 A2 | 11/2004 |
| WO | WO 2005/097695 A2 | 10/2005 |
| WO | WO 2010/055146 A2 | 5/2010 |
| WO | WO 2010/060868 A1 | 6/2010 |
| WO | WO 2011/121057 A1 | 10/2011 |
| WO | WO 2011/121058 A1 | 10/2011 |

OTHER PUBLICATIONS

U.S. Appl. No. 13/128,594, filed May 10, 2011, Ercan Uenveren, et al.
U.S. Appl. No. 13/129,985, filed May 18, 2011, Johannes Eicher, et al.
Murthy, J. Krishna, et al—"Sol-gel-fluorination synthesis of amorphous magnesium fluoride", Journal of Solid State Chemistry, 2006, 179, 3, pp. 739-746; 8 pgs.
Kemnitz, Erhard, et al—"Amorphous Metal Fluorides with Extraordinary High Surface Areas", Angewandte Chemie, 2003, 42, pp. 4251-4254; 4 pgs.
Rudiger, Stephan, et al—"Non-aqueous sol-gel synthesis of nanostructured metal fluorides", Journal of Fluorine Chemistry, 2007, 128, 4, pp. 353-368; 16 pgs.
Kemnitz, Erhard, et al—"Erfolg durch internationale Forschungskooperation", Humboldt Spektrum, 2006, pp. 14-20; Abstract provided in English, 8 pgs.
Burton, D. J., et al—"Preparation of E-1,2,3,3,3-pentafluoropropene, Z-1,2,3,3,3-pentafluoropropene and E-1-iodopentafluoropropene", Journal of Fluorine Chemistry, 1989, 44, 1, pp. 167-174; 8 pgs.

* cited by examiner

*Primary Examiner* — Sudhakar Katakam
(74) *Attorney, Agent, or Firm* — Osha Liang LLP

(57) ABSTRACT

Halogenated alkenes, especially fluorinated alkenes can be prepared from halogenated and fluorinated alkanes, respectively, by dehydrohalogenation or dehydrofluorination in the presence of a high-surface metal fluoride or oxifluoride. Preferably, trifluoroethylene, pentafluoropropene, tetrafluorobutenes or trifluorobutadiene are prepared. Aluminum fluoride is highly suitable. The metal fluoride or oxifluoride can be applied supported on a carrier.

26 Claims, No Drawings

PREPARATION OF HALOGEN AND HYDROGEN CONTAINING ALKENES OVER METAL FLUORIDE CATALYSTS

CROSS-REFERENCE TO RELATED APPLICATIONS

This application is a U.S. national stage application under 35 U.S.C. §371 of International Application No. PCT/EP2008/059112 filed Jul. 11, 2008, which claims priority to European Patent Application No. 07112446.5 filed Jul. 13, 2007 and to European Patent Application No. 07112445.7 filed Jul. 13, 2007, these applications being incorporated herein by reference in their entirety for all purposes.

A transformation of saturated halogenated, especially fluorinated C-2, C-3, C-4 and C-5 alkanes into haloolefines, especially fluoroolefines, by dehydrohalogenation, especially dehydrofluorination, is of industrial as well as of ecological importance. Chloroolefines and fluoroolefines are intermediates in chemical synthesis. Trifluoroethylene, for example, can be polymerized. Fluoropropenes, for example, tetrafluoropropene and pentafluoropropene, are also suitable as intermediates in chemical synthesis. Further, the isomers of tetrafluoropropene and the isomers of pentafluoropropene, optionally in admixture with other compounds or additives, can be applied as blowing agent for preparation of plastic foams, as fire extinguishing agents or as refrigerants, for example, in mobile air conditioning ("MAC"). U.S. Pat. No. 7,091,388 discloses the preparation of pentafluoropropene by treating chloropentafluoropropane or hexafluoropropane with caustic or thermally over supported transition metal halides or oxides or bulk transition metal oxides. According to the examples disclosed therein, $CF_3$—$CH$=$CF_2$ (HFC-1225zc) is produced from 1,1,3,3,3-pentafluoro-1-chloropropane (HFC-235fa) or 1,1,1,3,3,3-hexafluoropropane (HFC-245fa). WO 2004/096737 describes that fluorobutenes and fluorobutadienes are suitable as monomers, as building blocks and as starting material for hydrofluorocarbons. This international patent application describes that specific butenes and butadienes can be prepared from 1,1,1,3,3-pentafluorobutane by thermal, basic or catalytic dehydrofluorination. Titanium, manganese, chromium, iron, cobalt, nickel, copper, zirconium, molybdenum, niobium, ruthenium, rhodium, palladium, silver, hafnium, tantalum, tungsten, rhenium, iridium, platinum and antimony are mentioned as suitable catalysts.

It is the objective of the present invention to provide a technically feasible process for the preparation of fluoroalkenes. It is another object of the present invention to provide a supported catalyst suitable for the process of the present invention. These objectives and other objectives are achieved by the present invention. In its broadest embodiment, the process of the present invention provides for the preparation of halogenated alkenes whereby a halogenated alkane with at least one hydrogen atom is dehydrohalogenated in the presence of X-ray amorphous high surface metal fluoride or X-ray amorphous or weakly crystalline metal oxide fluoride wherein the metal is selected from the 2, 3 or 4 main group or any subgroup of the periodic system of elements.

In one embodiment, the catalyst is a full catalyst. In another embodiment, the catalyst is carried on a support.

Lewis-acidic metal fluorides are preferred, especially aluminium fluorides, chromium fluorides and iron fluorides. Aluminium fluoride and aluminium oxyfluoride are preferred as catalyst. Aluminium fluoride is especially preferred as catalyst (if desired, carried on a support).

In the context of the present invention, the terms "amorphous" and "X-ray amorphous" are interchangeable. The metal fluorides have certain novel characteristics when compared with fluorides of the state of the art. They preferably have an active surface of about 100-300 $m^2/g$ (measured with $N_2$, e.g. in a micromeritics ASAP 2001). They are strong Lewis acids. They are essentially free of Cl. The amorphous metal fluoride is X-ray amorphous. The term "X-ray amorphous" denotes that the microcrystalline domains of the solid matter, i.e. the amorphous metal fluoride, have a size of less than 20 nm. They have a mesoporous surface, as revealed by REM (Reflection Electron Microscopy). These features especially apply to amorphous aluminium fluoride. The amorphous aluminium fluoride has a strongly distorted structure of the $AlF_3$ octahedron. These disorders are responsible for the X-ray amorphous condition of the solid matter. The quadrupol coupling constant is about 1.5 MHz. In the IR spectrum, rather only a single very broad band ($v_3$ of Al—F at 667 $cm^{-1}$) is observed as can be allocated to the amorphous rather the crystalline structure. The increased Lewis acidity can be demonstrated by pyridine absorption and $NH_3$-TPD ($NH_3$ temperature programmed desorption). The X-ray amorphous catalysts, especially $AlF_3$, have the advantage that they are not hygroscopic.

In the following, reference is made to the dehydrohalogenation process of the present invention. It is clear for the expert that the description thereof concerns the use of the above mentioned full catalyst as well as the above mentioned supported catalyst.

The terms "hydrofluoroalkanes" and "hydrofluoroalkenes" denote molecules which consist of fluorine, hydrogen and carbon. The terms "chloroalkanes" and "chloroalkenes" denote compounds which consist of chlorine and carbon, the terms "hydrochloroalkanes" and "hydrochloroalkenes" denote compounds which consist of chlorine, hydrogen and carbon. The terms "hydrochlorofluoroalkanes" and "hydrochlorofluoroalkenes" denotes compounds which consist of chlorine, fluorine, hydrogen and carbon. The terms "chlorofluoroalkanes" and "chlorofluoroalkenes" denote compounds consisting of chlorine, fluorine, and carbon. The term "perfluoroalkenes" denotes compounds consisting of fluorine and carbon. This scheme for alkene compounds analogously applies to alkadiene compounds.

For example, chlorinated alkenes or hydrochloroalkenes can be produced from hydrochloroalkanes. Chlorofluoroalkenes or hydrochlorofluoroalkenes can be produced from hydrochlorofluoroalkanes, and fluoroalkenes or hydrofluoroalkenes or fluoroalkenes can be produced from hydrofluoroalkanes or hydrofluorochloroalkanes with 1 chlorine atom. It is clear for the expert that hydrofluoroalkanes can produce fluoroalkenes (i.e., perfluoroalkenes) if only one hydrogen atom is present which is split off in the form of HF, or if two hydrogen atoms are split off as HF; in the latter case, an alkadiene is produced. If the hydrofluoroalkane starting material has more than one hydrogen atom, then one hydrogen atom is split off as HF, the other hydrogen atom or hydrogen atoms remain in the molecule, and thus, a hydrofluoroalkene is produced. Preferably, the alkane starting material (and thus, also the produced alkene) has 2 to 5 carbon atoms. Preferably, the number of chlorine atoms and/or fluorine atoms in the halogenated alkane is equal to or higher than the number of hydrogen atoms, provided at least one hydrogen atom is comprised. Preferably, hydrochlorofluoroalkanes with one chlorine atom or more preferably hydrofluoroalkanes are applied as starting material, and consequently, hydrofluoroalkenes or fluoroalkenes are produced by dehydrofluorination or dehydrochlorination, respectively. Especially preferably, a hydrofluoroalkane is transformed to a hydrofluoroalkene, a fluoroalkene, a hydrofluoroalkadiene or a fluoroalkadiene. In view of this preferred embodiment, the invention will be described in detail.

The preferred process of the present invention provides for the preparation of fluorinated alkenes and comprises a step of dehydrofluorination of a hydrofluoroalkane with at least 1 hydrogen atom in the presence of an X-ray amorphous high surface aluminium fluoride catalyst or in the presence of an X-ray amorphous high surface aluminium fluoride catalyst carried on a support.

According to a preferred embodiment, fluorinated alkenes with 2 to 5 carbon atoms are produced from alkanes which have one hydrogen atom and one fluorine atom more than the produced alkene. According to another preferred embodiment, fluorinated alkadienes are produced from alkanes which have two hydrogen atoms and two fluorine atoms more than the fluorinated alkadiene. The terms "fluorinated alkenes" and "fluorinated alkadienes" denote compounds which consist of fluorine and carbon and which optionally comprise also 1 or more hydrogen atoms. Principally, fluorinated alkanes can be applied as starting compounds which comprise at least one fluorine atom; or hydrochlorofluoroalkanes with 1 chlorine atom and at least one fluorine atom; or, if fluorinated alkadienes are to be produced, hydrochlorofluoroalkanes with 1 or 2 chlorine atoms and 2 hydrogen atoms. If an alkadiene is produced, then, depending on the starting material, 2 HCl molecules, 2 HF molecules or 1 molecule of each are split off. Preferably, fluorinated alkanes are applied as starting compounds wherein the number of fluorine atoms is equal to or higher than the number of hydrogen atoms. For example, cis- and trans-1,1,1,2,4,4,5,5,5-nonafluoropentene-2, cis- and trans-1,1,1,3,4,4,5,5,5-nonafluoropentene-2 can be prepared from 1,1,1,2,3,4,4,5,5,5-decafluoropentane.

Preferably, perfluoroalkenes or perfluoroalkadienes with 2 to 4 carbon atoms are produced. Very preferably, hydrofluoroalkenes or hydrofluoroalkadienes with 2 to 4 carbon atoms are produced.

According to one preferred embodiment, alkenes with 2 or 3 carbon atoms are prepared. For example, tetrafluoropropenes can be prepared by dehydrofluorination of a pentafluoropropane. Especially preferably, pentafluoropropenes are prepared by dehydrofluorination of hexafluoropropanes. Especially preferably, HFC-1225ye is prepared by dehydrofluorination of 1,1,1,2,3,3-hexafluoropropane or 1,1,1,3,3,3-hexafluoropropane; or trifluoroethene is prepared by dehydrofluorination of 1,1,1,2-tetrafluoroethane. The dehydro fluorination reaction takes place very selectively—also in view of stereochemistry—and in high yields. The temperature at which dehydrochlorination or dehydrofluorination occurs depends from the respective starting compound and if it concerns a dehydrochlorination or a dehydrofluorination. Generally, the reaction temperature is equal to or higher than 50° C., preferably equal to or higher than 150° C. The reaction can be performed at even lower temperature, but in some cases, the speed of reaction may be considered to be too low. Generally, the reaction is performed at a temperature equal to or lower than 500° C., preferably equal to or lower than 450° C., and very preferably equal to or lower than 420° C. The catalyst is very active for extended periods of time when the reaction temperature is equal to or lower than 400° C. The result of the dehydrochlorination or dehydrofluorination is very good at temperatures e.g. above 400° C. The long-term performance of the catalyst is especially good if it is operated at temperatures equal to or below 400° C.

For dehydrofluorination, the reaction temperature is preferably equal to or higher than 200° C. The speed of reaction can be accelerated if the reaction temperature is equal to or higher than 250° C. Often, performing the reaction in a range of 300° C. to 400° C. allows a high reaction speed with high conversion. A fast reaction and high conversion are observed even if the dehydrofluorination temperature is equal to or higher than 400° C. It may be equal to or lower than 500° C.

In some cases, the balance between high reaction speed and high selectivity may favour operation at relatively low reaction temperature. For example, as demonstrated in an example, the dehydrofluorination of 1,1,1,2,3,3-hexafluoropropane, if performed at a temperature of 250° C., yields selectively the (Z) isomer of 1,1,1,2,3-pentafluoropropene which is the preferred isomer when applied as such, for example, as refrigerant, solvent, fire extinguishant or foam blowing agent because it is the more stable one. On the other hand, if obtaining mixtures of the (E) and (Z) isomers is acceptable, a higher reaction temperature will be selected because of the higher reaction speed.

Compounds which can be produced are for example:
fluoroethene from 1,1-difluoroethane
1,1,2-trifluoroethene from 1,1,2,2-tetrafluoroethane or 1,1,1,2-tetrafluoroethane
1,1,3,3-pentafluoropropene (HFC-1225zc) from 1,1,1,3,3,3-hexafluoropropane
1,2,3,3,3-pentafluoropropene from 1,1,1,2,3,3-hexafluoropropane
Cis- and trans-1,2,3,3-tetrafluoropropene and 1,1,2,3-tetrafluoropropene from 1,1,2,2,3-pentafluoropropane
Cis- and trans-1,3,3,3-tetrafluoropropene and 1,1,3,3-tetrafluoropropene from 1,1,1,3,3-pentafluoropropane
2,3,3,3-tetrafluoropropene from 1,1,1,2,2-pentafluoropropane
1,1,2-trifluoroethene from 1,1,2-trifluoro-2-chloroethane
1,1,1,3,3-pentafluoropropene from 1,1,1,3,3-pentafluoro-3-chloropropane or 1,1,1,3,3-pentafluoro-2-chloropropane.

According to another preferred embodiment, hydrofluoroalkanes with 4 carbon atoms and 1 to 9 fluorine atoms are dehydrofluorinated. For example, 1,1,2,3,3,4,4-heptafluorobutene can be produced from 1,1,2,2,3,3,4,4-octafluorobutane. It is preferred to treat C4 hydrofluoroalkanes with 4, 5 or 6 fluorine atoms and 6, 5 or 4 hydrogen atoms, respectively, in the dehydrofluorination reaction of the present invention.

Especially preferably in this embodiment, 1,1,1,3,3-pentafluorobutane is dehydrofluorinated. In a lower temperature range, predominantly one molecule of HF splits off from one molecule 1,1,1,3,3-pentafluorobutane. At higher temperatures, 2 molecules split off, and besides the butenes, also 1,1,3-trifluorobutadiene is formed.

To produce tetrafluorobutenes from 1,1,1,3,3-pentafluorobutane, the temperature at dehydrofluorination is equal to or higher than 50° C., preferably equal to or higher than 100° C., especially preferably equal to or higher than 180° C. Preferably, it is equal to or lower than 420° C. The temperature can even be higher, up to 500° C. If it is desired to produce the $C_4F_4H_4$ with low $C_4F_3H_3$ formation, the temperature is preferably equal to or lower than 260° C. To produce $C_4F_4H_4$ with a low content of the isomer with the lowest retention time in the gas chromatogram, the reaction is preferably performed at a temperature equal to or higher than 400° C. To produce trifluorobutadiene (often besides tetrafluorobutenes), the temperature is preferably equal to or higher than 260° C., preferably equal to or higher than 350° C. Often, the temperature is here equal to or less than 420° C. If, caused by too high temperatures, an undesired catalyst deactivation is observed, the temperature is reduced respectively.

In the dehydrofluorination reaction of 1,1,1,3,3-pentafluorobutane, isomers are produced, namely 2,4,4,4-tetrafluoro-1-butene and (E) and (Z) 1,1,1,3-tetrafluoro-2-butenes. They have different boiling points and can be separated by distillation. If two molecules of HF are split off, 1,1,3-trifluorobutadiene is formed.

The expert is aware that the dehydrofluorination reaction can be performed within the temperature ranges given above with good yield. He is aware that often, he can perform the reaction at even lower temperatures, but with lower yield. He is also aware that he can perform the reaction at higher temperatures than those given above; often, the yield per time unit is better, but sometimes the selectivity may become lower, or, if 1,1,1,3,3-pentafluorobutane is dehydrofluorinated, the molar ratio of butane products may vary. Trifluorobutadiene is produced in good yield at temperatures equal to or higher than 350° C., but it forms even at lower temperatures.

If one observes diminishing catalyst activity, e.g. after long reaction periods, or if the reaction temperature was selected too high, a regeneration of the catalyst is possible. Oxidizing gases can be passed at elevated temperatures through the reactor, e.g. air or oxygen. As is described below, the catalytic activity can be extended by passing a hydrofluorocarbon/nitrogen (or inert gas) mixture through the reactor.

The reaction can be performed batch wise or continuously. It is preferred to operate in the gas phase, especially continuously.

If desired, the halogenated hydrocarbon can be diluted before the dehydrohalogenation reaction with an inert gas, for example, nitrogen, or a noble gas, for example, argon. In this case, the halogenated hydrocarbon preferably is present in the gas mixture with inert gas in an amount of equal to or more than 10 vol.-%. Preferably, it is present in an amount of equal to or less than 75 vol.-%, more preferably in an amount of equal to or less than 50 vol.-%, and especially preferably equal to or less than 35 vol.-%. The productivity of the catalyst was observed to be higher when using inert gas (nitrogen for example).

In another aspect of the present invention mixtures comprising or consisting of nitrogen and a hydrofluorocarbon with 2 to 5 carbon atoms in a molar ratio of $N_2$: hydrofluorocarbon of (2-9):1, preferably of (3-6):1 are passed over the catalyst. Mixtures comprising or consisting of nitrogen and a hydrofluorocarbon with 2 to 5 carbon atoms in a molar ratio of $N_2$:hydrofluorocarbon of (3-5):1 are especially preferred. Especially preferred are mixtures comprising or consisting of $N_2$ and a C3 or C4 hydrofluorocarbon in a molar ratio of (2-9):1, preferably (3-6):1, more preferably (3-5):1. Most preferred are mixtures consisting of $N_2$ and pentafluoropropane, hexafluoropropane, pentafluorobutane or hexafluorobutane. In this embodiment, the hydrofluorocarbon is especially preferably 1,1,1,2,3,3-hexafluoropropane, 1,1,1,3,3,3-hexafluoropropane, 1,1,1,2,3,3-hexafluoropropane or, most preferred, 1,1,1,3,3-pentafluorobutane. Mixtures consisting of nitrogen and 1,1,1,3,3-pentafluorobutane in a molar ratio of $N_2$: 1,1,1,3,3-pentafluorobutane of (2-9):1, preferably (3-6):1, most preferably 3-5):1 are especially preferred.

Without intending to limit the invention to this explanation, it is assumed that the surface of the catalyst, by the sweep of inert gas, is kept relatively free from molecules, e.g. HF, which may block or otherwise influence the acidic centres of the catalyst.

The resulting product gas mixture comprises the produced haloalkene, hydrogen halide, e.g. HCl or HF, and often also starting compound or haloalkadiene. If the starting compound was entered into the reaction in diluted form, also the diluent gas will be contained in the product gas mixture. The work up can be performed in a known manner. For example, the product gas mixture can be passed through a wet washer (a washer operated with water, optionally containing a base, for example, sodium hydroxide, sodium carbonate, sodium hydrogen carbonate, calcium hydroxide, or calcium carbonate, or even an amine) and/or a dry agent, for example, KF or NaF to remove HF or HCl. The gases passing the washer can be condensed in a cooled trap to condense product and starting compound. They can be separated by known technique, for example, pressure distillation or deep temperature distillation.

Also in some other reactions, for example, the dehydrofluorination of 1,1,1,2,3,3-hexafluoropropane or 1,1,1,3,3-pentafluorobutane, the product may be obtained in the form of isomers. No separation of the isomers is needed if an isomer mixture suits the intended use. If a separation of the isomers appears desirable, this can often be achieved by methods known in the art. Sometimes, these isomers can be separated by distillation. In other cases, the undesired isomer can be converted into the other isomer. For example, in case of the dehydrofluorination of 1,1,1,2,3,3-hexafluoropropane, a mixture of (Z) and (E) isomers of HFC-1225ye is obtained. While this (E)/(Z) mixture can be applied as refrigerant, as solvent or for any other purposes, the (Z) isomer appears to be the preferred one because it is more stable than the (E) isomer. If desired, the (E) isomer can be converted to the (Z) isomer as described by D. J. Burton, T. D. Spawn, P. L. Heinze, A. R. Bailey and S. Shin-Ya in J. Fluorine Chemistry 44 (1989), pages 167 to 174 by contacting it with $SbF_5$.

According to one preferred aspect of the present invention, a process is provided which comprises the steps of preparing mixtures of the (E) isomer and the (Z) isomer of $CF_3$—CF=CHF (HFC-1225ye) according to the invention and a subsequent step of treating these mixtures with $SbF_5$ or with UV light to convert the (E) isomer into the (Z) isomer. In this way, the (Z) isomer of HFC-1225ye is provided which is essentially free of the (E) isomer without the need for distillation or other separation processes. The term "essentially" denotes preferably that the (Z) isomer of HFC-1225ye comprises equal to or less than 5% by weight, preferably, equal to or less than 3% by weight of the (E) isomer.

Recycling of unreacted starting material or unwanted reaction product to the dehydrofluorination reactor is possible. Often, for example, when 1,1,1,3,3-pentafluorobutane is dehydrofluorinated, several reaction products are obtained, especially, tetrafluorobutenes and trifluorobutadiene. If trifluoributadiene is the desired product, the fluorobutenes formed can be recycled to the dehydrofluorination reactor.

In the following, the synthesis of the catalyst is described.

The X-ray amorphous high surface metal fluoride, which preferably is aluminium fluoride ("HS—$AlF_3$"; it is one of the strongest solid Lewis acids at all) can be applied as full catalyst (or "bulk" catalyst), or in the form of a coating on a support. In the following, the full or bulk catalyst, in view of the preferred metal fluoride, HS—$AlF_3$, is described in detail.

The synthesis of the high surface area aluminium fluoride (HS—$AlF_3$), as well as of other high surface are metal fluorides, can be performed as described in US 2006/0052649 or EP 1440939 A1 (method for the preparation of amorphous metal fluorides), and EP 1666411 A1 (method for the preparation of X-ray amorphous or weakly crystalline metal oxide fluorides and new uses thereof). Amorphous metal fluoride is preferred. It can be prepared as described in EP 1440939 A1. Amorphous high surface area aluminium fluoride (or other high surface area metal fluorides) is prepared by a method comprising the steps of a) providing a precursor, whereby the precursor comprises a structure having a formula of $M^{x+}F_{(x-\delta)-y}B_yL_d$; and b) reacting the precursor with a fluorinating agent generating the amorphous metal fluoride having a formula of $M^{x+}F_{x-\delta}$);

whereby M is a metal of the $2^{nd}$, $3^{rd}$ or $4^{th}$ main group or any metal from a sub-group of the periodic system of the elements, preferably aluminium; B is a co-ordinately bound group; x is in case of aluminium 3; y is any integer between 1 and 3; δ is 0 to 0.1; and x-δ>y.

B is preferably an alkoxide, enolate or carboxylic acid group, more preferably an alkoxide of the formula —O—$C_cH_{2c+1}$ wherein c is any integer from 1 to 6; L is a solvent, preferably an anhydrous organic solvent selected from the group comprising alcohols, ethers, ketones, alkanes, aromatics; and d is ≦1.

According to EP 1440939 A1, the precursor is obtained by reacting $M^{x+}B_x$, wherein B is preferably an alkoxide, if the metal M is aluminium, B is more preferably propoxide, dissolved or suspended in an organic solvent L, with 2 to 4 equivalents, preferably 3 equivalents, anhydrous HF, preferably dissolved in an organic solvent L', whereby L' can be any of the solvents L and also L' can be equal to L; followed by removing excessive solvents under vacuum at temperatures equal to or less than 350° C., preferably equal to or less than 200° C., still more preferably equal to or less than 100° C.; providing a precursor as defined above.

The preparation of the precursor is preferably performed in a water free solvent, preferably selected from the group consisting of alcohols, ethers, ketones, alkanes, petroleum ether, formic acid, acetic acid or propionic acid. Alcohols of formula $C_cH_{2c+1}OH$ with c=1 to 6, especially 1 to 3, are preferred.

The precursor obtained thereby, in a second step, is further fluorinated, "activated", whereby gaseous fluorinating agents are used at elevated temperatures, preferably hydrofluorocarbons or hydrofluorochlorocarbons, especially $CHClF_2$ or, still more preferably, $CH_2F_2$ at temperatures between up to 350° C., or gaseous HF at temperatures from 50° C. up to 300° C., preferably at 75° C. up to 150° C. The fluorinating agent is preferably admixed with an inert gas such as nitrogen or argon, whereby up to 95% by volume inert gas can be used; providing an amorphous metal fluoride as defined above, whereby in case of activation with HF the obtained metal fluoride, specifically if the metal is aluminium, can contain adsorbed HF, which can be removed by subsequent exposure to an inert gas stream at temperatures up to 250° C.

In a preferred embodiment, the amorphous high surface metal fluoride consists essentially of aluminium fluoride. The term "essentially" denotes preferably that the content of other amorphous metal fluorides is equal to or less than 3% by weight, still more preferably equal to or less than 2% by weight.

EP 1440939 A1 discloses another embodiment wherein $M^{x+}F_{(x-\delta)-y}B_y$ is used as starting material, and which is not coordinated with a solvent.

In another embodiment, if desired, the aluminium fluoride can be doped with metal fluorides of zinc, tin, copper, chromium, vanadium, iron, or magnesium.

The amorphous metal fluoride obtained has an extraordinary high surface area, preferably in the range of 100 to 300 $m^2/g$, as measured according to the BET method using $N_2$ (see [0091] of US 2006/052649 A1 for details, e.g. suitable apparatus for determination of the specific surface) and in case of Lewis acidic metal ions an unusual high Lewis acidity, which in case of aluminium fluoride, HS—$AlF_3$, equals that of $SbF_5$.

Details and examples for the preparation of high surface area metal fluorides are given in EP 1440939 A1.

Amorphous aluminium fluoride is the preferred metal fluoride. The process of the present invention yields the dehydrohalogenated products in good yield and good selectivity.

The amorphous metal fluoride, especially $AlF_3$, carried on a support, is highly suitable for application in the above described process of the present invention.

High surface X-ray amorphous metal fluoride on a support, preferably with the exception of $MgF_2$ as support, is novel and another aspect of the present invention. The supported highly Lewis acidic catalysts the catalytic activity of which for the tested dehydro fluorination reactions are similar to that of the known bulk catalyst (which is not concerned in the context of the present invention). In principle, the metal can be selected from the $2^{nd}$, $3^{rd}$ or $4^{th}$ 4 group or the sub groups of the periodic system of the elements. Of course, if desired, the supported catalyst may comprise mixed amorphous metal fluorides. Preferred amorphous metal fluorides are those of Al, Cr, Fe, V, Ga and Mg. Amorphous aluminium fluoride is the preferred metal fluoride also for the supported catalysts. Preferably, a support is selected which has a suitably shaped form, is chemically and thermally stable under the conditions of catalyst synthesis and under reaction conditions of catalyst use, mechanically stable, not deteriorating the performance of the catalyst, not interfering with the catalysed reaction, and enabling anchoring of HS—$AlF_3$. Any support which meets these requirements can be used. For example, oxides, fluorides and oxifluorides of aluminium or of transition metals are very suitable. Usually, these are present in crystalline form. Activated carbon can also be applied; in a preferred embodiment, aluminium oxide or aluminium fluoride is used as support; in a more preferred embodiment aluminium oxide is used, and in an even more preferred embodiment γ-$Al_2O_3$ is used as support. In this case, the supported metal fluoride is high surface metal fluoride on γ-$Al_2O_3$.

Very preferably, the supported amorphous metal fluoride catalyst is HS—$AlF_3$ on a support, e.g., HS—$AlF_3$ on γ-$Al_2O_3$. If desired, the aluminium fluoride can be doped with one or more other metal fluorides, for example, the fluorides of zinc, tin, copper, iron, chromium, vanadium or magnesium. Such doped supported catalysts can be prepared by adding hydrolysable metal compounds, for example, the metal alkoxides to the hydrolysable aluminium compound.

Preferably, the total amount of coated amorphous metal fluoride, especially of $AlF_3$ in the supported catalyst is equal to or greater than 3% by weight, more preferably equal to or more than 4% by weight. Preferably, the content of aluminium fluoride in the supported catalyst is equal to or less than 30% by weight, more preferably equal to or less than 20% by weight. In some applications, the content can be equal to or less than 10% by weight. A range with good results, e.g. in dehydrofluorination reactions, is between 4 and 20% by weight. A range of 4 to 8% by weight also gives good results.

In the following, the preparation of amorphous metal fluorides, especially amorphous aluminium fluoride (HS—$AlF_3$), supported on a carrier, will be described. The terms "carrier" and "support" are interchangeable in the frame of the present invention.

The synthesis of the high surface area aluminium fluoride (HS—$AlF_3$), coating, as well as coatings of other high surface are metal fluorides, can be performed analogously as described in US 2006/0052649 or EP 1440939 A1 (method for the preparation of amorphous metal fluorides), and EP 1666411 A1 (method for the preparation of X-ray amorphous or weakly crystalline metal oxide fluorides and new uses thereof). A coating of amorphous metal fluoride as described in EP 1440939 A1 is preferred. In a preferred embodiment, the amorphous high surface metal fluoride consists essentially of aluminium fluoride. The term "essentially" denotes preferably that the content of other amorphous metal fluorides in the coating is equal to or less than 3% by weight, still more preferably equal to or less than 2% by weight.

The synthesis of supported high surface area metal fluoride on a support, preferably aluminium fluoride on a support (HS—AlF$_3$/support) follows basically the synthesis route outlined for HS—AlF$_3$ in EP 1440939 A1 extended for a step of anchoring to a suitable support at an appropriate stage of HS—AlF$_3$ synthesis.

It is known from EP 1666411 A1 that the Lewis acidity of amorphous high surface area aluminium fluoride becomes reduced upon partial substitution of fluoride by oxide, consequently, if formation of oxyfluoride is to be avoided, reducing adsorbed water and/or inherent OH-groups of the support by thermal pre-treatment preserves the Lewis acidity, i.e. the catalytic performance of the anchored HS—AlF$_3$, i.e. of the final catalyst. Therefore, the support, e.g. γ-Al$_2$O$_3$, is preferably heated prior to the coating procedure. Heating is preferably performed for equal to or less than 48 hours, preferably equal to or less than 12 hours, advantageously at temperatures which do not result in undesired transformation of the support. For example, it is avoided to transform γ-Al$_2$O$_3$ into α-Al$_2$O$_3$ (which can be determined by X-ray powder diffraction). For example, γ-Al$_2$O$_3$ can be heated to temperatures between 400° C. and 900° C. Preferably, it is heated to a temperature equal to or higher than 600° C. Preferably, it is heated to a temperature equal to or lower than 900° C. in air and subsequently cooled down to room temperature under exclusion of moisture.

According to this aspect of the present invention, amorphous high surface area metal fluoride is prepared by a method comprising the steps of
a) providing a precursor coated on a support, whereby the precursor comprises a structure having a formula of $M^{x+}F_{(x-\delta)-y}B_yL_d$; and
b) reacting the precursor with a fluorinating agent generating the amorphous metal fluoride having a formula of $M^{x+}F_{x-\delta}$ on a support;
whereby M is a metal of the 2$^{nd}$, 3$^{rd}$ or 4$^{th}$ main group or any metal from a sub-group of the periodic system of the elements, preferably aluminium; B is a co-ordinately bound group; x is in case of aluminium 3; y is any integer between 1 and 3; δ is 0 to 0.1; and x-δ>y.

B is preferably an alkoxide, enolate or carboxylic acid group, more preferably an alkoxide of the formula —O—C$_c$H$_{2c+1}$ wherein c is any integer from 1 to 6; L is a solvent, preferably an anhydrous organic solvent selected from the group comprising alcohols, ethers, ketones, alkanes, aromatics; and d is ≦1. In one embodiment, d is 0.

The preparation of the supported precursor is preferably performed in a waterfree solvent, preferably selected from the group consisting of alcohols, ethers, ketones, alkanes, petroleum ether, formic acid, acetic acid or propionic acid. Alcohols of formula C$_c$H$_{2c+1}$OH with c=1 to 6, especially 1 to 3, are preferred.

The precursor can be obtained by reacting $M^{x+}B_x$, wherein B is preferably an alkoxide, if the metal M is aluminium, B is more preferably propoxide, dissolved or suspended in an organic solvent L, with anhydrous HF, preferably dissolved in an organic solvent L', whereby L' can be any of the solvents L and also L' can be equal to L. This is a sol-gel type reaction.

The method to apply a coating of the precursor on the support will now be explained in detail for the preferred embodiment of amorphous aluminium fluoride as supported catalyst.

The coating procedure can be performed in a manner principally known to prepare catalytic coatings on catalyst supports. Two specific alternatives are preferred. Both alternatives comprise a step a) or—as concerns the second alternative—b) wherein a support coated with the precursor $M^{x+}F_{(x-\delta)-y}B_yL_d$ or $M^{x+}F_{(x-\delta)-y}B_y$ is formed, and a step c) wherein the activation takes place.

Alternative a): According to the first preferred alternative, the support is impregnated with the aluminium compound $M^{x+}B_x$; M, B, x and y have the meanings given above. After impregnation, the sol-gel reaction with HF, preferably applied in a solvent, is performed to obtain the precursor.

In detail, the support, preferably thermally pretreated γ-Al$_2$O$_3$, is given, preferably under stirring, to a solution of a suitable organic aluminium compound, preferably an aluminium alkoxide, more preferably aluminium isopropoxide or methoxide, in an anhydrous organic solvent, preferably an alcohol. If a doped supported catalyst is to be produced, a suitable organic metal compound of the respective metal or metals is added. Contact between support and aluminium compound, preferably under stirring, is continued for a sufficient time to achieve the desired degree of impregnation. For example, after addition of the aluminium compound, the contact can be continued for equal to or more than 10 minutes, preferably, for equal to or more than 20 minutes. The contact can be extended, if desired, to a very long time, for example, more than 6 hours. It is assumed that the longer the contact, the deeper the aluminium compound or precursor will penetrate into the support. Preferably, the contact between support and aluminium compound is equal to or less than 6 hours, still more preferably, equal to or less than 2 hours. Often, 20 minutes to 45 minutes are very suitable.

Then, $M^{x+}B_x$, (here, M is preferably Al) is reacted with HF to transform it into the precursor. A solution of anhydrous hydrogen fluoride in an organic solvent, preferably in an C1 to C3 alcohol or in diethyl ether, is added, preferably under continued stirring, to the system of support and aluminium compound $M^{x+}B_x$ (M=Al). The amount of HF is selected so that the molar ratio of HF:Al is preferably equal to or greater than 2. Preferably, it is equal to or lower than 4. Very preferably, the molar ratio of HF:Al is 3±0.1. Most preferably, the molar ratio is 3. Preferably, the total amount of aluminium compound starting material (which is converted to the HS—AlF$_3$ phase) in the system is adjusted to correspond to an AlF$_3$ content of the final catalyst of equal to or greater than 3% by weight, more preferably equal to or more than 4% by weight. Preferably, the content of aluminium fluoride in the supported catalyst is equal to or less than 30% by weight, more preferably equal to or less than 20% by weight, sometimes even equal to or less than 10% by weight. Often, the amount is adjusted so that the content of the HS—AlF3 phase in the supported catalyst is between A highly preferred range is between 4 and 20% by weight. Often, a supported catalyst with 4 to 8% by weight HS—AlF$_3$ is produced.

Alternative b) According to the second preferred alternative, the organic metal compound, preferably the aluminium compound, preferably in the form of a solution, is first reacted in the sol-gel type reaction with the appropriate amount of HF solution, preferably under stirring, followed by addition of the respective support, whereby the materials used and their relative amounts are as described above, especially in view of the alternative a).

After the reaction of the aluminium compound and HF to form the precursor has taken place, be it after impregnation of the carrier according to the first alternative, or before contact with the carrier according to the second alternative, excessive solvent(s) is or are removed. Preferably, this is performed in a gentle manner, preferably under vacuum. The removal advantageously is supported by warming or heating. Preferably, the temperature is equal to or higher than 25° C., more preferably, it is equal to or higher than 30° C. Preferably, the temperature is equal to or lower than ≦200° C., more preferably, it is equal to or lower than 150° C. A preferred range is 40 to 90° C. Both procedures a) or b) and subsequent solvent removal provide a supported precursor, which, if γ-Al$_2$O$_3$ is used as support, can be described best by the formula of M$^{x+}$F$_{(x-\delta)-y}$B$_y$L$_d$/γ-Al$_2$O$_3$, or, according to the other embodiment of EP 1440939, is M$^{x+}$F$_{(x-\delta)-y}$B$_y$/γ-Al$_2$O$_3$, with M, F, x, y, δ, B, L and d as given above.

The precursor already has catalytic activity. The catalytic activity can be greatly enhanced if the precursor is activated by subsequent fluorination with a gaseous fluorinating agent at elevated temperature, for example, with one or more hydrochlorofluorocarbons or hydrofluorocarbons, especially with 1 or 2 carbon atoms, or with HF. The fluorinating agent is preferably admixed with an inert gas such as nitrogen or argon, whereby 10 up to 95 vol % inert gas can be used. In a preferred manner, the activation is performed applying
A1) CHClF$_2$ or CH$_2$F$_2$ or CHF$_3$ or CH$_3$F, or
A2) gaseous HF; followed optionally by
B) flushing with inert gas, preferably nitrogen or a noble gas, for example, argon,
providing a highly Lewis acidic supported HS—AlF$_3$ catalyst, preferably on γ-Al$_2$O$_3$ of the formula AlF$_{3-\delta}$/γ-Al$_2$O$_3$.

In step A1), CHClF$_2$ is the preferred fluorinating agent. It can be applied in admixture with preferably mixed with up to 95% (v/v), of an inert gas such as nitrogen or a noble gas, preferably argon; the content of the inert gas is preferably equal to or higher than 75% (v/v); it is preferably equal to or lower than to 90% (v/v). Especially preferably, the inert gas content is 83±2% (v/v). The temperature in step A1) preferably is equal to or higher than 250° C., more preferably, equal to or higher than 300° C. Preferably, the temperature is equal to or lower than 400° C. 340° C. to 360° C. is a very preferred range.

In the alternative step A2) wherein HF is used as fluorinating agent, the temperature during treatment is preferably equal to or lower than 200° C.; preferably, it is equal to or higher than 90° C. A temperature range from 75° C. to 150° C. is very preferred, still more a range from 110° C. to 130° C. HF preferably is diluted with equal to or more than 80% (v/v) of an inert gas, for example, nitrogen or a noble gas, preferably argon. Preferably, the inert gas content is equal to or less than 97.5% (v/v). An especially preferred content of inert gas is in the range of 95±2% (v/v) of inert gas.

In step B), flushing is optionally performed to remove volatiles from the catalyst. It is preferred to perform a flushing step. Flushing can be stopped when the desired degree of purification has been achieved. It can be performed for an extended time, for example, up to ten hours or more. Preferably, flushing is performed for equal to or less than 6 hours. Preferably, it is performed for equal to or more than 1 hour. The temperature during flushing is preferably equal to or higher than 200° C. Preferably, it is equal to or lower than 300° C. A temperature range between 240° C. and 260° C. is very suitable. This is especially advantageous if the activation was performed using HF.

Oxyfluorides on a support can be prepared as described in WO 2006/058794. It includes a step of converting the precursor into an X-ray amorphous oxide/hydroxyfluoride. This conversion can be performed by hydrolysis or thermal treatment of the precursor if it contains a metal-oxygen bond.

It is to be noted that the manufacture of supported catalysts according to the present invention as described herein is also applicable to other metal fluorides and especially to mixtures of different metal fluorides resulting in doped systems.

The supported catalyst can be prepared in the form of a powder, in the form of pellets, beads, extrudates and other formed bodies. Beads with a diameter in the range of, for example, 1 to 10 mm are very suitable for the dehydrofluorination process.

The supported amorphous metal fluoride obtained has an extraordinary high surface area, preferably in the range of 100 to 300 m$^2$/g, as measured according to the BET method using N$_2$ (see [0091] of US 2006/052649 A1 for details) and in case of Lewis acidic metal ions an unusual high Lewis acidity, which in case of aluminium fluoride, HS—AlF$_3$, equals that of SbF$_5$.

The supported metal catalyst, optionally doped, can be applied in many fields. For example, it can be for halogen exchange reactions, especially for the chlorine-fluorine exchange of chlorohydrocarbons or chlorofluorohydrocarbons, for example, with 1 to 5 carbon atoms. It also can be used for other reactions where Lewis acid catalysts are applicable. It can be used for isomerisation reactions of haloperfluoroalkanes, for the isomerisation of olefins, e.g. for the isomerisation of alkenes-1 to alkenes-2, for the catalysis of Friedel-Crafts acylation reactions as well as Friedel-Crafts alkylation reactions of aromatic ring systems. Especially preferably, the supported catalyst is applied in the dehydrohalogenation process of the present invention.

Another aspect of the present invention are mixtures comprising or consisting of nitrogen and a hydrofluorocarbon with 2 to 5 carbon atoms in a molar ratio of N$_2$: hydrofluorocarbon of (2-9):1, preferably of (3-6):1. Mixtures comprising or consisting of nitrogen and a hydrofluorocarbon with 2 to 5 carbon atoms in a molar ratio of N$_2$:hydrofluorocarbon of (3-5):1 are especially preferred. Especially preferred are mixtures comprising or consisting of N$_2$ and a C3 or C4 hydrofluorocarbon in a molar ratio of (2-9):1, preferably (3-6):1, more preferably (3-5):1. Most preferred are mixtures consisting of N$_2$ and pentafluoropropane, hexafluoropropane, pentafluorobutane or hexafluorobutane. In this embodiment, the hydrofluorocarbon is especially preferably 1,1,1,2,3,3-hexafluoropropane, 1,1,1,3,3,3-hexafluoropropane, 1,1,1,2,3,3-hexafluoropropane or, most preferred, 1,1,1,3,3-pentafluorobutane. Mixtures consisting of nitrogen and 1,1,1,3,3-pentafluorobutane in a molar ratio of N$_2$: 1,1,1,3,3-pentafluorobutane of (2-9):1, preferably (3-6):1, most preferably 3-5):1 are especially preferred.

In the foregoing embodiment, the term "comprising" preferably denotes compositions comprising the mixtures in an amount of at least 70% by weight. The remainder to 100% by weight can, for example, be recycled reaction mixture, optionally after separating off certain components. For example, if it is intended to produce 1,1,3-trifluorobutadiene, one can remove selectively the 1,1,3-trifluorobutadiene and can recycle unreacted 1,1,1,3,3-pentafluorobutane starting material and the tetrafluorobutenes.

These gas (or vapour) mixtures are especially suitable for catalytic gas phase dehydrofluorination reactions, especially when an aluminium fluoride catalyst is used because it was observed that catalytic centres of the catalyst remain active in the presence of the reaction product hydrogen fluoride. Without intention to be limited by this explanation, it is assumed that the nitrogen removes HF molecules adhering to the catalyst surface, thus reducing the catalytic activity.

Another aspect of the present invention is to use nitrogen or inert gas in admixture with a hydrofluoroalkane compound to remove HF from the surface of dehydrofluorination catalysts in gas phase reactions, especially for aluminium fluoride catalysts. Of course, it may occur that other compounds adhering to the catalyst surface are also removed. The gas (or vapour) mixtures can be produced before their introduction into a reactor, e.g. they can be prepared by mixing the components in a storage tank under pressure, or they can be produced in situ in the reactor.

The invention will be explained further by the following examples 1 to 9 without intending to limit it.

General Procedure for Catalytic Dehydrofluorination of HFCs

A stainless steel or fused silica tube reactor (8 mm ID, 380 mm length) was loaded with powdery HS—AlF$_3$ (catalyst A), prepared as described in EP 1440939. The bed of catalyst was held in the middle of the vertical reactor by a plug of silver or quartz wool. Dehydrofluorination experiments were performed passing the respective N$_2$ diluted HFC gas (HFC: N$_2$=1:4; total flow 2.5 mL/min) at the indicated temperature through the reactor, the gaseous effluents were passed through sodium fluoride pellets or aqueous potassium hydroxide solution to scrub HF and then analysed online by GC (Shimadzu GC 17A with Porapak Q capillary column). In separate experiments the products identified by GC were confirmed by $^1$H- and $^{19}$F-NMR of there solutions in CDCl$_3$.

EXAMPLE 1

Dehydrofluorination of 1,1,1,2-tetrafluoroethane over catalyst A

Following the General Procedure the dehydrofluorination of 1,1,1,2-tetrafluoroethane, CF$_3$—CFH$_2$ (R134a), was performed using 0.8 g catalyst. The formation of trifluoroethylene as result of the dehydrofluorination over the catalyst was investigated at different temperatures, followed by on-line GC and confirmed by $^1$H and $^{19}$F NMR spectroscopy.

|  | Temperature, °C.: | | |
| --- | --- | --- | --- |
|  | 200 | 250 | 300 |
| Conversion, %: | | | |
| CF$_3$—CFH$_2$ | 1.0 | 6.2 | 10.8 |
| Selectivity, % | | | |
| CF$_2$=CFH | 30.6 | 71.2 | 89.0 |

EXAMPLE 1.1

Dehydrofluorination of 1,1,1,2-tetrafluoroethane over catalyst A in a micro plant scale Example 1 was repeated. This time, 20.25 g of the catalyst were placed in a tube with 1 inch ID (inner diameter). The HFC-134a was supplied to the tube with a flow 10.5 to 13 l/h, N$_2$ was supplied with 7.1 l/h.

Content of HFC-1123 in the raw gas leaving the reactor:

| Example No. | Reaction temperature | Content HFC-1123 in the raw gas |
| --- | --- | --- |
| 1.1.1 | 300° C. | 1.26 mass % |
| 1.1.2 | 350° C. | 1.85 mass % |
| 1.1.3 | 400° C. | 13.15 mass % |
| 1.1.4 | 450° C. | 33.15 mass % |
| 1.1.5 | 500° C. | 30.21 mass % |

The productivity fell in the course of several hours, especially at higher temperatures.

EXAMPLE 2

Dehydrofluorination of 1,1,1,2,3,3-hexafluoropropane

Following the General Procedure, the dehydrofluorination of 1,1,1,2,3,3-hexafluoropropane, CF$_3$—CFH—CHF$_2$ (HFC 236ea), was performed using 0.7 g of catalyst. The results of the dehydrofluorination over the catalyst at different temperatures were followed by on-line GC and confirmed by $^1$H and $^{19}$F NMR Spectroscopy.

|  | Temperature, °C.: | | |
| --- | --- | --- | --- |
|  | 250 | 300 | 350 |
| Conversion, %: | | | |
| CF$_3$—CFH—CHF$_2$ | 7 | 19 | 95 |
| Selectivity, % | | | |
| CHF=CF—CF$_3$ (Z) | 100 | 89 | 88 |
| CHF=CF—CF$_3$ (E) | 0 | 11 | 12 |

EXAMPLE 3

Dehydro fluorination of 1,1,1,3,3,3-hexafluoropropane

Following the General Procedure, the dehydrofluorination of 1,1,1,3,3,3-hexafluoropropane, CF$_3$—CH$_2$—CF$_3$ (R 236fa) was performed using 0.62 g catalyst. The results of the dehydrofluorination over the catalyst at different temperatures were followed by on-line GC and confirmed by $^1$H and $^{19}$F NMR Spectroscopy.

|  | Temperature, °C.: | | |
| --- | --- | --- | --- |
|  | 300 | 350 | 400 |
| Conversion, %: | | | |
| CF$_3$—CF$_2$—CFH$_2$ | 3 | 13.5 | 33.5 |
| Selectivity, % | | | |
| CF$_3$—CH=CF$_2$ | 9 | 88 | 66 |

Examples Using a Supported Catalyst

EXAMPLE 4

Manufacture of γ-Al$_2$O supported HS—AlF$_3$ precursor

Firstly, γ-Al$_2$O$_3$ (10 g, pellets 3 mm diameter), calcined at 900° C. in air for 12 hours whereby according to X-ray diffraction analysis no conversion to α-Al$_2$O$_3$ was detectable, was added to a stirred solution of aluminium triisopropoxide (Al(O$^i$Pr)$_3$) (1.2 g) in water free isopropanol (15 mL). Stirring continued for about 0.5 hours, then 18 mMol hydrogen fluoride dissolved in water free isopropanol (6 mL) were added and for about another 1.5 hours stirred. The mixture was then placed in a rotary evaporator and at 70° C. under vacuum the solvent removed yielding about 11 g γ-Al$_2$O supported HS—AlF$_3$ precursor.

EXAMPLE 5

Manufacture of γ-Al$_2$O supported HS—AlF$_3$ (HS—AlF$_3$/γ-Al$_2$O$_3$)

Supported precursor prepared according to example 4 (about 2 g) was loaded into a vertical stainless steel tube reactor on a silver wool plug. A mixture of CHClF$_2$ (4 mL/min) and N$_2$ (20 mL/min) was passed through the sample and the temperature of the reactor was slowly increased up to 250° C. After altogether 6 hours the reactor was cooled down and about 1.9 catalyst, corresponding to 4.9% HS—AlF$_3$ loading on the Al$_2$O$_3$, was taken out under exclusion of moisture.

EXAMPLE 6

Catalytic activity of a catalyst comprising γ-Al$_2$O supported HS—AlF$_3$ (HS—AlF$_3$/γ-Al$_2$O$_3$)

As test reaction the catalytic isomerisation of 1,2-dibromohexafluoropropane to 2,2-dibromohexafluoropropane was studied, which has to be catalysed by the strongest known Lewis acids (SbF$_5$, ACF, HS—AlF$_3$). About 20 mg of HS—AlF$_3$/γ-Al$_2$O$_3$ was placed under exclusion of moisture in a small glass vessel equipped with a magnetic stirrer bar and sealed with a rubber cap. Through the rubber cap, about 300 μL CBrF$_2$CBrFCF$_3$ were added with a syringe, and the mixture was stirred at room temperature for 2 hours. Then was a small amount of the liquid removed from the vessel, mixed with CDCl$_3$ and subjected to 19F-NMR analysis. The analysis showed that 30% of CBrF$_2$CBrFCF$_3$ was converted to CF$_3$CBr$_2$CF$_3$.

General Procedure for Catalytic Dehydrofluorination of HFCs

A stainless steel or fused silica tube reactor (8 mm ID, 380 mm length) was loaded with HS—AlF$_3$ supported by γ-Al$_2$O$_3$ which was prepared as described in example 2 above. The bed of catalyst was held in the middle of the vertical reactor by a plug of silver or quartz wool. Dehydrofluorination experiments were performed passing the respective N$_2$ diluted HFC gas (HFC:N$_2$=1:4; total flow 2.5 mL/min) at the indicated temperature through the reactor, the gaseous effluents were passed through sodium fluoride pellets or aqueous potassium hydroxide solution to scrub HF and then analysed online by GC (Shimadzu GC 17A with Porapak Q capillary column). In separate experiments the products identified by GC were confirmed by $^1$H- and $^{19}$F-NMR of there solutions in CDCl$_3$.

EXAMPLE 7

Dehydrofluorination of 1,1,1,2-tetrafluoroethane over the supported catalyst Following the General Procedure the dehydrofluorination of 1,1,1,2-tetrafluoroethane, CF$_3$—CFH$_2$ (R134a), was performed using 2 g of the supported catalyst. The results of the dehydrofluorination over the catalyst at different temperatures were followed by on-line GC and confirmed by $^1$H and $^{19}$F NMR Spectroscopy.

|  | Temperature, ° C.: | | |
| --- | --- | --- | --- |
|  | 200 | 250 | 300 |
| Conversion, %: | | | |
| CF$_3$—CFH$_2$ | 1.1 | 5.8 | 12.2 |
| Selectivity, % | | | |
| CF$_2$=CFH | 24.6 | 68.9 | 83.7 |

EXAMPLE 8

Dehydrofluorination of 1,1,1,2,3,3-Hexafluoropropane over the supported catalyst Following the General Procedure, the dehydrofluorination of 1,1,1,2,3,3-hexafluoropropane, CF$_3$—CFH—CHF$_2$ (R 236ea), was performed using 1.97 g of the supported catalyst. The results of the dehydrofluorination over the catalyst at different temperatures were followed by on-line GC and confirmed by $^1$H and $^{19}$F NMR Spectroscopy

|  | Temperature, ° C.: | | |
| --- | --- | --- | --- |
|  | 250 | 300 | 350 |
| Conversion, %: | | | |
| CF$_3$—CFH—CHF$_2$ | 7 | 19 | 95 |
| Selectivity, % | | | |
| CHF=CF—CF$_3$ (Z) | 100 | 89 | 88 |
| CHF=CF—CF$_3$ (E) | 0 | 11 | 12 |

EXAMPLE 9

Dehydrofluorination of 1,1,1,3,3-pentafluorobutane

A catalyst was used which was prepared as described above in example 4. It contained 15% by weight of HS—AlF$_3$, supported on Al$_2$O$_3$ beads with a diameter of about 3 mm.

A tube with 8 mm internal diameter, containing 0.76 g of the catalyst, was used as reactor; height of the catalyst in the tube: 4 cm. A mixture of HFC-365mfc and nitrogen, molar ratio $N_2$:HFC-365mfc kept at about 5, was passed through the reactor at a given temperature.

The results measured by GC-MS are compiled in the following table. The content of the different compounds is given in area-% of the GC:

| Temperature | $C_4F_5H_5$ | $C_4F_4H_4$[1] | $C_4F_4H_4$[2] | $C_4F_4H_4$[3] | $C_4F_3H_3$[4] |
|---|---|---|---|---|---|
| 307° C. | 7.7 | 27.8 | 40.9 | 20.8 | 1.5 |
| 347° C. | 6.9 | 24.5 | 36.5 | 19.4 | 8.6 |

[1] Allocated to (E) 1,1,1,3-tetrafluoro-but-2-ene, shortest retention time in the GC
[2] Allocated to 2,4,4,4-tetrafluoro-1-butene
[3] Allocated to (Z) 1,1,1,3-tetrafluoro-but-2-ene, longest retention time in the GC
[4] 1,1,3-trifluorobutadiene The reaction was performed for several hours at 257° C. and then several hours at 350° C. The composition of the raw gas was essentially constant for the respective reaction temperature.

NMR data for 2,4,4,4-tetrafluorobutene:

$^{13}$C: $CF_3$ δ=125.1 ppm (q); $CH_2$ δ=35.3 ppm; $\underline{CF}$ δ=150.1 ppm; $\underline{CH}_2$=CF δ=35.3 ppm $^1$H: $\overline{CH}_2$ δ=3.17 ppm (dq); CH (cis to F on C2 atom) δ=5.04 ppm (dd); CH (trans to F on $\overline{C2}$ atom) δ=4.54 ppm (dd)

Example 4 was repeated in the micro pilot plant with respective higher productivity using 19.9 g catalyst A. The volumetric gas flow was between 31 and 37 l/h. The results were comparable in view of the composition of the raw gas. The data determined by GC-MS at several different temperatures are compiled in the following table:

| Temperature | $C_4F_5H_5$ | $C_4F_4H_4$[1] | $C_4F_4H_4$[2] | $C_4F_4H_4$[3] | $C_4F_3H_3$[4] |
|---|---|---|---|---|---|
| 207° C. | 52.2 | 14.4 | 23 | 8.9 | 0.0 |
| 257° C. | 20.7 | 26.3 | 36.6 | 15.6 | 0.3 |
| 325° C. | 15.7 | 26.7 | 38.1 | 17.5 | 1.6 |
| 350° C. | 12.7 | 23.2 | 33.5 | 17.3 | 10.5 |
| 405° C. | 7.8 | 9.4 | 50.3 | 9.5 | 15.4 |

[1] Allocated to (E) 1,1,1,3-tetrafluoro-but-2-ene, shortest retention time in the GC
[2] Allocated to 2,4,4,4-tetrafluoro-1-butene by $^1$H and $^{13}$C NMR
[3] Allocated to (Z) 1,1,1,3-tetrafluoro-but-2-ene, longest retention time in the GC
[4] 1,1,3-trifluorobutadiene.

The invention claimed is:

1. A process for the preparation of halogenated alkenes from halogenated alkanes wherein the halogenated alkane which comprises at least one hydrogen atom is dehydrohalogenated in the presence of an X-ray amorphous metal fluoride catalyst or in the presence of an X-Ray amorphous or semicrystalline metal oxy fluoride catalyst wherein the metal is selected from the group consisting of the $2^{nd}$ main group, the $3^{rd}$ main group, the $4^{th}$ main group or any sub group of the periodic system of elements wherein the amorphous metal fluoride catalyst has a surface area ranging from 100 to 300 m²/g.

2. The process according to claim 1 wherein the halogenated alkene has from 2 to 5 carbon atoms.

3. The process according to claim 2 wherein the halogenated alkene has from 3 to 5 carbon atoms.

4. The process according to claim 1 wherein the halogenated alkene is a fluorinated alkene.

5. The process according to claim 4 wherein the alkene is a fluorinated alkene which consists of carbon and fluorine atoms, or a hydrofluoroalkene which consists of carbon atoms, fluorine atoms and at least one hydrogen atom.

6. The process according to claim 4 wherein the alkene is a trifluoroethene, a tetrafluoropropene, a pentafluoropropene, a tetrafluorobutene or a trifluorobutadiene.

7. The process according to claim 1 wherein the halogenated alkane is a hydrofluoroalkane or a hydrochlorofluoroalkane with one chlorine atom.

8. The process according to claim 1 wherein trifluoroethene is prepared by dehydrofluorination of 1,1,1,2-tetrafluoroethane or dehydrochlorination of 1,1,2-trifluoro-1-chloroethane, or wherein tetrafluoropropene is prepared by dehydrofluorination of pentafluoropropane or dehydrochlorination of chlorotetrafluoropropane, or wherein (Z)-1,1,1,2,3-pentafluoropropene is prepared from 1,1,1,2,3,3-hexafluoropropane or 1,1,1,2,3-pentafluoro-3-chloropropane, or wherein 1,1,1,3,3-pentafluoropropene is prepared by dehydrofluorination of 1,1,1,3,3,3-hexafluoropropane or dehydrochlorination of 1,1,1,3,3,-pentafluoro-2-chloropropane or 1,1,1,3,3-pentafluoro-3-chloropropane, or wherein 2,4,4,4-tetrafluoro-1-butene and (E) and (Z) 1,1,1,3-tetrafluoro-2-butenes are produced by dehydrofluorination of 1,1,1,3,3-pentafluorobutane, or wherein 1,1,3-trifluorobutadiene is produced by dehydrofluorination of 1,1,1,3,3-pentafluorobutane.

9. The process according to claim 1 wherein the dehydrohalogenation reaction is performed at a temperature equal to or higher than 50° C. and equal to or lower than 450° C.

10. The process according to claim 1 wherein the halogenated alkane is introduced into a dehydrohalogenation reactor in the form of its mixture with $N_2$, with a molar ratio of $N_2$:halogenated alkane of (2-9):1.

11. The process according to claim 1 wherein the amorphous high surface metal fluoride or amorphous or semicrystalline oxy fluoride is coated on a support to form a supported catalyst.

12. The process according to claim 1 Wherein the metal is aluminium.

13. The process according to claim 1 wherein the halogenated alkane is a hydrofluorocarbon with 2 to 5 carbon atoms, and wherein a mixture comprising of nitrogen and said hydrofluorocarbon with 2 to 5 carbon atoms is used in the dehydrohalogenation reaction in a molar ratio of $N_2$:hydrofluorocarbon of (2-9):1.

14. The process according to claim 13 wherein the mixture consists of nitrogen and 1,1,1,3,3-pentafluorobutane in a molar ratio of $N_2$: 1,1,1,3,3-pentafluorobutane of (2-9): 1.

15. The process according to claim 1 wherein the halogenated alkane is dehydrohalogenated in the presence of a supported, X-ray amorphous high surface area aluminium fluoride supported on activated carbon or γ-$Al_2O_3$.

16. The process according to claim 1, wherein the halogenated alkane is dehydrohalogenated in the presence of a supported, X-ray amorphous high surface area metal fluoride catalyst which is obtained in a method comprising the steps of
   a) providing a precursor coated on a support, wherein the precursor comprises a structure having a formula of $M^x+F_{(x-\delta)-y}B_yL_d$; and
   b) reacting the precursor with a fluorinating agent generating the X-ray amorphous metal fluoride having a formula of $M^x+F_{(x-\delta)}$ on the support; wherein M is a metal of the $2^{nd}$, $3^{rd}$ or $4^{th}$ main group or any metal from a sub-group of the periodic system of the elements; B is a co-ordinately bound organic group; x is 3 in case of M being aluminium; y is any integer between 1 and 3; δ is 0 to 0.1; d≦1 including 0, and x−δ>y, with the proviso that $MgF_2$ is excluded as support.

17. The process according to claim 16 whereby the precursor coated on the support is provided by providing a compound $M^X+B_X$, wherein B is the co-ordinately bound organic group, and a) impregnating the support with the compound $M^X+B_X$, and performing a reaction with HF to provide the precursor coated on the support, or h) reacting the compound $M^X+B_X$ with HF to provide the precursor, and contacting the precursor with the support to provide the precursor coated on the support.

18. The process according to claim 9 wherein the dehydrohalogenation reaction is performed at a temperature equal to or lower than 400° C.

19. The process according to claim 13 wherein the mixture comprises nitrogen and said hydrofluorocarbon with 2 to 5 carbon atoms in a molar ratio of $N_2$:hydrofluorocarbon of (3-6):1.

20. The process according to claim 14, wherein the mixture consists of nitrogen and 1,1,1,3,3-pentafluorobutane in a molar ratio of $N_2$:1,1,1,3,3-pentafluorobutane of (3-6):1.

21. The process according to claim 11 wherein $MgF_2$ is excluded as support in the supported catalyst.

22. The process according to claim 17 wherein the coordinately bound organic group is an alkoxide with 1 to 5 carbon atoms.

23. The process according to claim 17 wherein the reaction in step (a) is performed with HF dissolved in an organic solvent.

24. The process according to claim 1 being carried out for the preparation of a mixture of isomers (E) and (Z) of 1,1,1,2,3-pentafluoropropene CF3-CF=CHF, and wherein the process further comprises a subsequent step of treating the mixture with $SbF_5$ or with UV light to convert the (E) isomer into the (Z) isomer, for the (Z) isomer of CF3-CF=CHF to comprise equal to or less than 5% by weight of the (E) isomer.

25. The process according to claim 1 wherein the high amorphous metal fluoride catalyst is regenerated by passing air or oxygen.

26. The process according to claim 10, wherein the use of nitrogen in the mixture extends catalytic activity or provides a higher catalytic activity than if no nitrogen is used.

* * * * *